United States Patent [19]

Hoffmann et al.

[11] 4,195,082
[45] Mar. 25, 1980

[54] COMBATING ARTHROPODS WITH 0-ALKYL-0-TRIFLUOROMETHYLSULPHONYLPHENYL-THIONO (THIOL)-PHOSPHORIC ACID ESTERS

[75] Inventors: Hellmut Hoffmann, Wuppertal; Erich Klauke, Odenthal; Ingeborg Hammann, Cologne, all of Fed. Rep. of Germany

[73] Assignee: Bayer Aktiengesellschaft, Leverkusen, Fed. Rep. of Germany

[21] Appl. No.: 883,078

[22] Filed: Mar. 3, 1978

[30] Foreign Application Priority Data

Mar. 30, 1977 [DE] Fed. Rep. of Germany ....... 2714038

[51] Int. Cl.² ................ A01N 9/36; C07F 9/165
[52] U.S. Cl. ..................... 424/216; 260/949
[58] Field of Search .................... 260/949; 424/216

[56] References Cited

U.S. PATENT DOCUMENTS

| | | | |
|---|---|---|---|
| 3,991,141 | 11/1976 | Berger et al. | 210/949 X |
| 4,067,972 | 1/1978 | Oswald et al. | 260/949 X |

FOREIGN PATENT DOCUMENTS 7301018   7/1873   Netherlands ............................. 424/216

*Primary Examiner*—Anton H. Sutto
*Attorney, Agent, or Firm*—Sprung, Felfe, Horn, Lynch & Kramer

[57] ABSTRACT

0-Alkyl-0-trifluoromethylsulphonylphenyl-thiono (thiol)-phosphoric acid esters and ester-amides of the formula

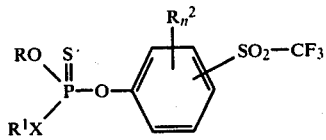

in which
R and $R^1$ each independently is alkyl,
$R^2$ is hydrogen, halogen, alkyl or nitro,
n is 1, 2, 3 or 4,
X is oxygen, sulphur or $NR^3$, and
$R^3$ is hydrogen or alkyl,
which possess arthropodicidal properties.

10 Claims, No Drawings

COMBATING ARTHROPODS WITH O-ALKYL-O-TRIFLUOROMETHYLSULPHONYL-PHENYL-THIONO (THIOL)-PHOSPHORIC ACID ESTERS

The present invention relates to and has for its objects the provision of particular new O-alkyl-O-trifluoromethylsulphonylphenyl-thiono (thiol)-phosphoric acid esters and ester-amides which possess arthropodicidal properties, active compounds in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is already known that certain trifluoromethylthio- and alkylthio-phenyl(thiono)-phosphoric(phosphonic) acid esters, for example O-ethyl-O-(2-methyl-4-trifluoromethylthiophenyl)-thionoethanephosphonic acid ester, O,O-dimethyl-O-(3-methyl-4-methylthio-phenyl)-thiono- and O,O-diethyl-O-(4-trifluoromethylthiophenyl)-phosphoric acid ester possess insecticidal and acaricidal properties (see German Auslegeschriften (German Published Specifications) Nos. 1,153,747 and 1,116,656).

The present invention now provides, as new compounds, the trifluoromethylsulphonylphenylthiono(thiol)-phosphoric acid esters and ester-amides of the general formula

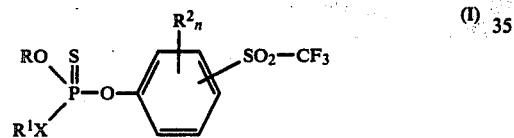

in which
R and $R^1$, which may be identical or different, each represent alkyl,
$R^2$ represents hydrogen, halogen, alkyl or nitro,
n represents 1, 2, 3 or 4 and
X represents oxygen, sulphur or the $NR^3$ group,
in which
$R^3$ represents hydrogen or alkyl.

Preferably, R represents straight-chain or branched alkyl with 1 to 6 (especially 1 to 3) carbon atoms, $R^1$ represents straight-chain or branched alkyl with 1 to 6 (especially 1 to 4) carbon atoms, $R^2$ represents hydrogen, chlorine or nitro, and X represents an oxygen or sulphur atom or the NH group, although it may also be $N-C_{1-4}$-alkyl.

Surprisingly, the trifluoromethylsulphonylphenylthiono(thiol)-phosphoric acid esters and ester-amides according to the invention exhibit a better insecticidal and acaricidal action than the trifluoromethylthio- and alkylthiophenyl(thiono)-phosphoric(phosphonic) acid esters of analogous structure, and of the same type of action, which were previously known from the literature. The compounds according to the present invention thus represent a genuine enrichment of the art.

The invention also provides a process for the preparation of a trifluoromethylsulphonylphenylthiono(thiol)-phosphoric acid ester or ester-amide of the formula (I) in which a thiono(thiol)-phosphoric(phosphonic) acid ester halide or ester-amide halide of the general formula

in which
R, $R^1$ and X have the above-mentioned meanings and
Hal represents halogen, preferably chlorine, is reacted, if appropriate in the presence of a solvent or diluent, with a trifluoromethylsulphonylphenol of the general formula

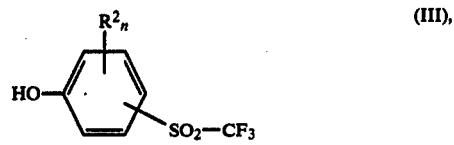

in which
$R^2$ and n have the above-mentioned meanings, the latter being employed in the form of an alkali metal salt, alkaline earth metal salt or ammonium salt or as such in the presence of an acid acceptor.

If, for example, 0-ethyl-S-sec.-butyl-thionothiolphosphoric acid diester chloride and 2-methyl-4-trifluoromethylsulphonyl-phenol are used as starting materials, the course of the reaction can be represented by the following equation:

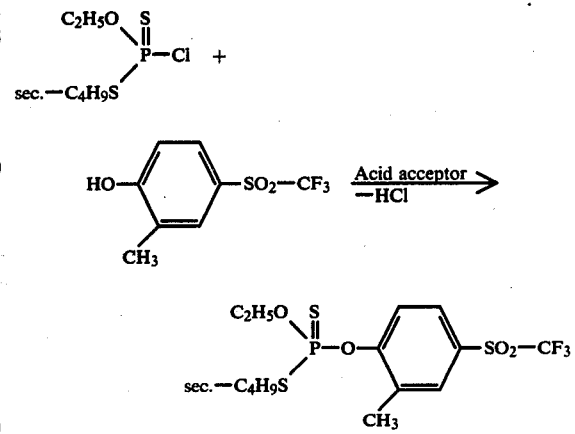

The thiono(thiol)-phosphoric acid ester halides and ester-amide halides (II) to be used as starting materials are known and can be prepared by known processes. The following may be mentioned as individual examples thereof: O,O-dimethyl-, O,O-diethyl-, O,O-di-n-propyl-, 0-methyl-O-ethyl-, O-methyl-O-n-propyl,O-methyl-O-iso-propyl-, O-methyl-O-n-butyl-, O-methyl-O-iso-butyl-, O-methyl-O-sec.-butyl-, O-methyl-O-tert.-butyl-, O-ethyl-O-n-propyl-, O-ethyl-O-iso-propyl-, O-ethyl-O-n-butyl-, O-ethyl-O--sec.-butyl-, O-ethyl-O-iso-butyl-, O-n-propyl-O-butyl- and O-iso-propyl-O-butyl-thionophosphoric acid diester chloride, and O,S-dimethyl-, O,S-diethyl-, O,S-di-n-propyl-, O,S-di-iso-propyl-, O-ethyl-S-n-propyl-, O-ethyl-S-iso-propyl-, O-ethyl-S-n-butyl-, O-ethyl-S-sec.-butyl-, O-n-propyl-S-ethyl-, O-n-propyl-S-iso-propyl-, O-methyl-S-n-propyl- and O-methyl-S-ethyl-thionothiolphosphoric acid diester chloride, as well as O-methyl-N-methyl-, O-methyl-N-ethyl-, O-methyl-N-n-propyl-, O-methyl-N-iso-propyl-, O-ethyl-N-methyl-, O-ethyl-N-ethyl-, O-ethyl-N-n-propyl-, O-ethyl-N-iso-propyl-, O-n-propyl-N-methyl-, O-n-propyl-N-ethyl-, O-n-propyl-N-n-propyl-, O-n-propyl-N-iso-propyl-, O-iso-propyl-N-methyl-, O-iso-propyl-N-ethyl-, O-iso-propyl-N-n-propyl-, O-iso-propyl-N-iso-propyl-, O-sec.-butyl-N-ethyl- and O-sec.-butyl-N-n-propyl-thionophosphoric acid monoester-amide chloride.

Trifluoromethylsulphonylphenols (III) to be used as starting materials are also known and can be prepared in accordance with processes known from the literature. The following may be mentioned as individual examples thereof: 4-trifluoromethylsulphonyl-phenol, 3-methyl-4-trifluoromethylsulphonyl-phenol, 2-methyl-4-trifluoromethylsulphonylphenol, 2-chloro-4-trifluoromethylsulphonyl-phenol, 3-chloro-4-trifluoromethylsulphonyl-phenol and 2-nitro-4-trifluoromethylsulphonyl-phenol.

The process for the preparation of the compounds according to the invention is preferably carried out in the presence of a suitable solvent or diluent. Virtually all inert organic solvents can be used for this purpose, especially aliphatic and aromatic, optionally chlorinated, hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

All customary acid-binding agents can be used as acid acceptors. Alkali metal carbonates and alkali metal alcoholates, such as sodium carbonate and potassium carbonate, sodium methylate and ethylate and potassium methylate and ethylate, have proved particularly suitable, as have aliphatic, aromatic or heterocyclic amines, for example triethylamine, trimethylamine, dimethylaniline, dimethylbenzylamine and pyridine.

The reaction temperature can be varied within a substantial range. In general, the reaction is carried out at from 0° to 100° C., preferably at from 15° to 70° C.

In general, the reaction is allowed to take place under normal pressure.

To carry out the process, the starting components are in most cases employed in stoichiometric amounts. An excess of either reactant produces no significant advantages. In most cases, the reactants are brought together in one of the above-mentioned solvents in the presence of an acid acceptor and are stirred, in most cases at elevated temperature, for one or more hours to complete the reaction. Thereafter, the reaction mixture is cooled, is poured into water and is extracted by shaking with an organic solvent, for example toluene. The organic phase is then worked up in the usual manner by washing, drying and distilling off the solvent.

The new compounds are obtained in the form of oils which, in a number of cases, cannot be distilled without decomposition, but are freed from the last volatile constituents by so-called "incipient distillation," that is to say by prolonged heating under reduced pressure to moderately elevated temperatures, and are purified in this manner. They are characterised by the refractive index.

As already mentioned, the compounds according to the present invention are distinguished by an excellent insecticidal and acaricidal activity. They are therefore active against plant pests, pests harmful to health and pests of stored products and combine a low phytotoxicity with a good action against sucking and biting insects and against mites.

For this reason, the compounds according to the invention can be employed successfully as pesticides in plant protection and in the hygiene field and the field of protection of stored products.

The compounds according to the present invention can also be used in the field of veterinary medicine.

The active compounds are well tolerated by plants, have a favorable level of toxicity to warm-blooded animals, and can be used for combating arthropod pests, especially insects and acarids, which are encountered in agriculture, in forestry, in the protection of stored products and of materials, and in the hygiene field. They are active against normally sensitive and resistant species and against all or some stages of development.

The abovementioned pests include:

from the class of the Isopoda, for example *Oniscus asellus*, Armadillidium vulgare and *Porcellio scaber;* from the class of the Diplopoda, for example *Blaniulus guttulatus;* from the class of the Chilopoda, for example *Geophilus carpophagus* and *Scutigera* spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis, Haematopinus* spp. and *Linoganathus* spp.;

from the order of the Mallophaga, for example *Trichodectes* spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lecturlarius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana*, Heliothis spp., *Laphygma exigua, Mamestra brassicae, Panolis flammea, Prodenia litura*, Spodoptera spp., *Trichoplusia ni, Carpocapsa pomonella*, Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnamina* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae*, Diabrotica spp., *Psylliodes chrysocephala, Epilachna varivestis*, Atomaria spp., *Oryzaephilus surinamensis*, Anthonomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster*, Musca spp., Fannia spp., *Calliphora erythrocephala*, Lucilla spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be use in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

It will be realized, of course, that the concentration of the particular active compound utilized in admixture with the carrier vehicle will depend upon the intended application. Therefore, in special cases it is possible to go above or below the aforementioned concentration ranges.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

The present invention also provides an arthropodicidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects or acarids) which comprises applying to the arthropods, or to a habitat thereof, a compound of the present invention alone or in the form of a composition containing as active ingredient a compound of the present invention in admixture with a diluent or carrier.

The present invention also provides a method of freeing or protecting domesticated animals from ectoparasitical insects or acarids which comprises applying to said animals a compound according to the present invention, in admixture with a diluent or carrier.

The preparation of the new compounds of the present invention is illustrated, without limitation, by the following example:

EXAMPLE 1

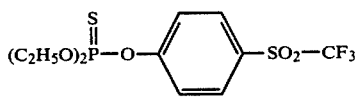
(1)

19 g (0.1 mol) of O,O-diethylthionophosphoric acid diester chloride were poured into a slurry of 23 g (0.1 mol) of 4-trifluoromethylsulphonyl-phenol and 15 g of potassium carbonate in 200 ml of acetonitrile. The reaction mixture was then stirred further for 3 hours at 60° C. and was cooled, poured into water and taken up in toluene, and the phases were separated off. The organic phase was washed with water and dried over sodium sulphate, the toluene was stripped off in vacuo and the residue was subjected to incipient distillation. 34 g (90% of theory) of O,O-diethyl-O-(4-trifluoromethylsulphonyl-phenyl)-thionophosphoric acid ester having a refractive index $n_D^{20}$ of 1.4900 were thus obtained.

The following compounds of the formula

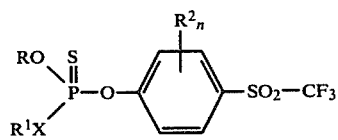
(Ia)

could be prepared analogously:

Table 1

| Compound No. | R | $R^1$ | $R_n^2$ | X | Refractive index: | Yield (% of theory) |
|---|---|---|---|---|---|---|
| 2 | $C_2H_5$ | $C_2H_5$ | 2-Cl | O | $n_D^{21}$:1,5009 | 74 |
| 3 | $C_2H_5$ | $n-C_3H_7$ | H | S | $n_D^{20}$:1,5213 | 83 |
| 4 | $C_2H_5$ | iso-$C_3H_7$ | H | NH | $n_D^{20}$:1,5012 | 82 |
| 5 | $CH_3$ | $CH_3$ | H | O | $n_D^{24}$:1,4953 | 80 |
| 6 | $CH_3$ | $CH_3$ | 2-Cl | O | $n_D^{21}$:1,5109 | 76 |
| 7 | $CH_3$ | $CH_3$ | 2-$NO_2$ | O | $n_D^{20}$:1,5145 | 64 |

O-n-Butyl-N,N-diethyl-O-(2-chloro-6-methyl-4-trifluoromethylsulphonyl-phenyl)-thionophosphoric acid ester-amide can be similarly prepared.

The insecticidal and acaricidal activity of the compounds of this invention is illustrated by the following examples wherein the compounds according to the present invention are each identified by the number (given in brackets) from Example 1 hereinabove.

The known comparison compounds are identified as follows:

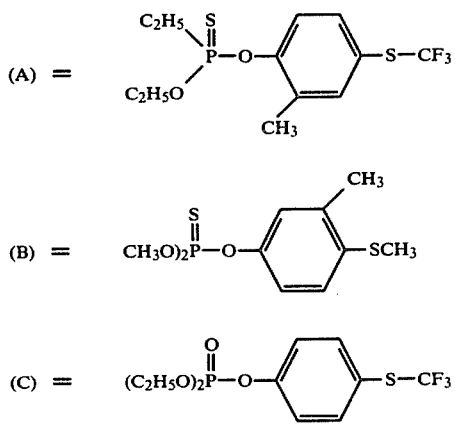

EXAMPLE 2

Myzus test (contact action)

Solvent: 3 parts by weight of acetone

Emulsifier: 1 part by weight of alkylaryl polyglycol ether

To produce a suitable preparation of active compound, 1 by weight of the active compound was mixed with the stated amount of solvent containing the stated amount of emulsifier and the concentrate was diluted with water to the desired concentration.

Cabbage plants (Brassica oleracea) which had been heavily infested with peach aphids (Myzus persicae) were sprayed with the preparation of the active compound until dripping wet.

After the specified periods of time, the degree of destruction was determined as a percentage: 100% meant that all of the aphids were killed whereas 0% meant that none of the aphids were killed.

The active compounds, the concentrations of the active compounds, the evaluation times and the results can be seen from the following table:

Table 2

| | (Insects which damage plants) Myzus test | |
|---|---|---|
| Active compounds | Active compound concentration in % | Degree of destruction in % after 1 day |
| (A) | 0.1 | 100 |
| | 0.01 | 0 |
| (5) | 0.1 | 100 |
| | 0.01 | 100 |
| (7) | 0.1 | 100 |
| | 0.01 | 100 |
| (1) | 0.1 | 100 |
| | 0.01 | 100 |
| (3) | 0.1 | 100 |
| | 0.01 | 100 |

EXAMPLE 3

Tetranychus test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were sprayed with the preparation of the active compound until dripping wet.

After the specified periods of time, the degree of destruction was determined as a percentage: 100% meant that all of the spider mites were killed whereas 0% meant that none of the spider mites were killed.

The active compounds, the concentrations of the active compounds, the evaluation times and the results can be seen from the following table:

Table 3

| | (Mites which damage plants) Tetranychus test | |
|---|---|---|
| Active compounds | Active compound concentration in % | Degree of destruction in % after 1 day |
| (B) | 0.1 | 0 |
| (C) | 0.1 | 0 |
| (A) | 0.1 | 0 |
| (2) | 0.1 | 90 |
| (3) | 0.1 | 90 |

It will be appreciated that the instant specification and examples are set forth by way of illustration and not limitation, and that various modifications and changes may be made without departing from the spirit and scope of the present invention.

What we claim is:

1. An O-alkyl-O-trifluoromethylsulphonylphenylthiono (thiol)-phosphoric acid ester or ester-amide of the formula

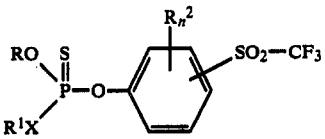

in which
R and R$^1$ each independently is alkyl,
R$^2$ in hydrogen, halogen, alkyl or nitro,
n is 1, 2, 3 or 4,
X is oxygen, sulphur or NR$^3$, and
R$^3$ is hydrogen or alkyl.

2. An ester according to claim 1, wherein
R is alkyl with 1 to 6 carbon atoms,
R$^1$ is alkyl with 1 to 6 carbon atoms,
R$^2$ is hydrogen, chlorine or nitro, and
X is oxygen, sulphur or NH.

3. An ester according to claim 1, wherein such ester is O,O-diethyl-O-(4-trifluoromethylsulphonyl-phenyl)-thionophosphoric acid ester of the formula

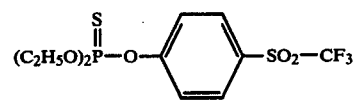

4. An ester according to claim 1, wherein such ester is O,O-diethyl-O-(2-chloro-4-trifluoromethylsulphonyl-phenyl)-thionophosphoric acid ester of the formula

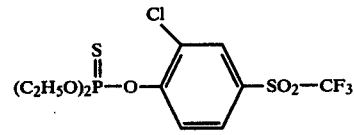

5. An ester according to claim 1, wherein such ester is O-ethyl-S-n-propyl-O-(4-trifuloromethylsulphonyl-phenyl)-thionothiolphosphoric acid ester of the formula

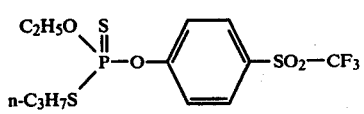

6. An ester according to claim 1, wherein such ester is O,O-dimethyl-O-(4-trifluoromethylsulphonyl-phenyl)-thionophosphoric acid ester of the formula

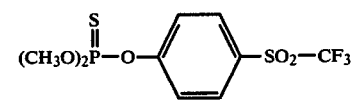

7. An ester according to claim 1, wherein such ester is O,O-dimethyl-O-(2-nitro-4-trifluoromethylsulphonyl-phenyl)-thionophosphoric acid ester of the formula

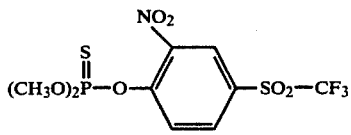

8. An arthropodicidal composition containing as active ingredient an arthropodicidally effective amount of an ester according to claim 1 in admixture with a diluent.

9. A method of combating arthropods which comprises applying to the arthropods, or to a habitat thereof, an arthropodicidally effective amount of an ester according to claim 1, in admixture with a diluent.

10. The method according to claim 9 wherein to a domesticated animal to be freed or protected from ectoparasitical insects or acarids there is applied O,O-diethyl-O-(4-trifluoromethylsulphonylphenyl)-thionophosphoric acid ester, O,O-diethyl-O-(2-chloro-4-trifluoromethyl-sulphonyl-phenyl)-thionophosphoric acid ester, O-ethyl-S-n-propyl-O-(4-trifluoromethylsulphonyl-phenyl)-thionothiolphosphoric acid ester, O,O-dimethl-O-(4-trifluoromethylsulphonyl-phenyl)-thiono-phosphoric acid ester or O,O-dimethyl-O-(2-nitro-4-trifluoromethylsulphonylphenyl)-thionophosphoric acid ester.

* * * * *